US008057537B2

(12) United States Patent
Zilla et al.

(10) Patent No.: US 8,057,537 B2
(45) Date of Patent: Nov. 15, 2011

(54) COMPLIANT VENOUS GRAFT

(75) Inventors: Peter P. Zilla, Capetown (ZA); Nasser Rafiee, Andover, MA (US); Deon Bezuidenhout, Capetown (ZA); Thomas Franz, Capetown (ZA); Mark Yeoman, Forest Row (GB); Hellmut Bowles, Bloubergrant (ZA); Nareak Douk, Lowell, MA (US); Michael F. Wolf, Golden Valley, MN (US)

(73) Assignee: Kips Bay Medical, Inc., Minneapolis, MN (US)

( * ) Notice: Subject to any disclaimer, the term of this patent is extended or adjusted under 35 U.S.C. 154(b) by 2051 days.

(21) Appl. No.: 10/834,360

(22) Filed: Apr. 28, 2004

(65) Prior Publication Data
US 2005/0070995 A1  Mar. 31, 2005

Related U.S. Application Data

(60) Provisional application No. 60/466,226, filed on Apr. 28, 2003.

(51) Int. Cl.
*A61F 2/90* (2006.01)
(52) U.S. Cl. .......................... 623/1.5; 623/1.13
(58) Field of Classification Search ............ 600/36; 623/1.13, 1.5
See application file for complete search history.

(56) References Cited

U.S. PATENT DOCUMENTS

| 3,797,485 | A | | 3/1974 | Urquhart |
| 4,173,689 | A | * | 11/1979 | Lyman et al. ............. 521/64 |
| 4,725,273 | A | * | 2/1988 | Kira ........................ 623/1.33 |
| 4,743,251 | A | | 5/1988 | Barra ............................ 623/1 |
| 4,834,746 | A | | 5/1989 | Kira |
| 4,921,495 | A | | 5/1990 | Kira |
| 4,956,178 | A | * | 9/1990 | Badylak et al. ............ 424/551 |
| 4,969,896 | A | | 11/1990 | Shors |
| 5,234,755 | A | | 8/1993 | Okamura |
| 5,320,100 | A | | 6/1994 | Herweck et al. |
| 5,413,598 | A | | 5/1995 | Moreland |
| 5,556,414 | A | | 9/1996 | Turi ............................ 606/198 |
| 5,584,876 | A | | 12/1996 | Bruchman |
| 5,645,581 | A | | 7/1997 | Zurbrugg ....................... 623/1 |
| 5,662,713 | A | * | 9/1997 | Andersen et al. ........... 128/898 |
| 5,681,345 | A | | 10/1997 | Euteneuer |
| 5,697,970 | A | | 12/1997 | Schmitt et al. |
| 5,700,287 | A | | 12/1997 | Myers et al. |

(Continued)

FOREIGN PATENT DOCUMENTS
DE      19910340      9/2000
(Continued)

OTHER PUBLICATIONS

Berry, "Hemodynamics and wall mechanics of a compliance matching stent: in vitro and in vivo analysis", Jan. 2002, PubMed, p. 1.*

(Continued)

*Primary Examiner* — Thomas J Sweet
*Assistant Examiner* — Rebecca Straszheim
(74) *Attorney, Agent, or Firm* — Haugen Law Firm PLLP

(57) ABSTRACT

A venous graft for replacement of a section of an artery and methods of making the graft. The graft comprises a flexible, resilient, generally tubular external support and a vein segment carried within and having an ablumenal surface in contact with and supported by the tubular support, the venous graft being capable of resilient radial expansion in a manner mimicking the radial compliance properties of an artery.

3 Claims, 8 Drawing Sheets

U.S. PATENT DOCUMENTS

| | | | |
|---|---|---|---|
| 5,716,395 A | | 2/1998 | Myers et al. |
| 5,728,150 A | | 3/1998 | McDonald et al. |
| 5,733,327 A | * | 3/1998 | Igaki et al. ............. 623/1.5 |
| 5,755,659 A | | 5/1998 | Zurbrugg |
| 5,769,884 A | | 6/1998 | Solovay |
| 5,824,047 A | | 10/1998 | Moreland ............. 623/1 |
| 5,900,433 A | | 5/1999 | Igo et al. |
| 5,910,168 A | | 6/1999 | Myers et al. |
| 5,913,894 A | | 6/1999 | Schmitt |
| 5,921,995 A | | 7/1999 | Klesbinski |
| 6,036,723 A | | 3/2000 | Anidjar et al. |
| 6,053,943 A | | 4/2000 | Edwin et al. |
| 6,071,306 A | | 6/2000 | Angelini ............. 623/1.13 |
| 6,077,298 A | | 6/2000 | Tu et al. ............. 623/1.19 |
| 6,113,612 A | | 9/2000 | Swanson et al. |
| 6,117,166 A | | 9/2000 | Winston et al. |
| 6,117,535 A | * | 9/2000 | Szycher et al. ............. 428/297.7 |
| 6,123,115 A | | 9/2000 | Greenhalgh ............. 139/196.1 |
| 6,159,239 A | | 12/2000 | Greenhalgh ............. 623/1.13 |
| 6,164,339 A | | 12/2000 | Greenhalgh ............. 139/1 R |
| 6,187,038 B1 | | 2/2001 | Sullivan et al. |
| 6,192,944 B1 | | 2/2001 | Greenhalgh ............. 139/425 R |
| 6,217,609 B1 | | 4/2001 | Haverkost |
| 6,264,684 B1 | | 7/2001 | Banas et al. ............. 623/1.13 |
| 6,293,965 B1 | | 9/2001 | Berg et al. |
| 6,309,413 B1 | | 10/2001 | Dereume et al. |
| 6,319,279 B1 | | 11/2001 | Shannon et al. |
| 6,331,191 B1 | | 12/2001 | Chobotov |
| 6,346,117 B1 | | 2/2002 | Greenhalgh ............. 606/200 |
| 6,358,275 B1 | | 3/2002 | McIlroy et al. |
| 6,364,895 B1 | | 4/2002 | Greenhalgh ............. 606/200 |
| 6,375,670 B1 | | 4/2002 | Greenhalgh ............. 606/200 |
| 6,391,037 B1 | | 5/2002 | Greenhalgh ............. 606/151 |
| 6,428,571 B1 | | 8/2002 | Lentz et al. |
| 6,485,513 B1 | | 11/2002 | Fan |
| 6,494,909 B2 | | 12/2002 | Greenhalgh ............. 623/1.24 |
| 6,551,352 B2 | | 4/2003 | Clerc et al. ............. 623/1.2 |
| 6,652,543 B2 | | 11/2003 | Spence et al. |
| 6,656,217 B1 | | 12/2003 | Herzog et al. |
| 6,709,455 B1 | | 3/2004 | Chouinard |
| 6,792,979 B2 | | 9/2004 | Konya et al. |
| 6,916,336 B2 | | 7/2005 | Patel et al. |
| 7,060,022 B2 | * | 6/2006 | Chen et al. ............. 600/36 |
| RE40,404 E | | 6/2008 | Schmitt et al. |
| 7,387,604 B2 | | 6/2008 | Case et al. |
| 7,452,374 B2 | | 11/2008 | Hain et al. |
| 7,481,836 B2 | | 1/2009 | Greenan |
| 7,575,592 B2 | | 8/2009 | Woo |
| 7,666,222 B2 | | 2/2010 | Wright et al. |
| 2002/0058992 A1 | | 5/2002 | Greenhaigh |
| 2002/0083820 A1 | | 7/2002 | Greenhaigh |
| 2003/0110830 A1 | * | 6/2003 | Dehdashtian et al. ............. 73/37 |
| 2003/0204249 A1 | | 10/2003 | Letort |
| 2004/0030348 A1 | | 2/2004 | Peterson et al. |
| 2004/0215309 A1 | | 10/2004 | Moritz |
| 2005/0004654 A1 | | 1/2005 | Khosravi et al. |
| 2005/0177224 A1 | | 8/2005 | Fogarty et al. |
| 2006/0052866 A1 | | 3/2006 | Gilles et al. |
| 2006/0069426 A1 | | 3/2006 | Weinberger |
| 2006/0149348 A1 | | 7/2006 | Vogel et al. |
| 2007/0055345 A1 | | 3/2007 | Arbefeuille |
| 2007/0198079 A1 | | 8/2007 | Casey et al. |
| 2008/0082160 A1 | | 4/2008 | Boyden et al. |
| 2009/0171436 A1 | | 7/2009 | Casanova et al. |

FOREIGN PATENT DOCUMENTS

| | | |
|---|---|---|
| RU | 2102016 | 1/1998 |
| WO | WO 96/38090 | 12/1996 |
| WO | WO 2004/096095 | 11/2004 |
| WO | WO2007035791 | 3/2007 |
| WO | WO2008118132 | 10/2008 |

OTHER PUBLICATIONS

Angelini, G.D., et al., An External, Oversized, Porous Polyester Stent Reduces Vein Graft Neointima Formation, Cholesterol Concentration, and Vascular Cell Adhesion Molecule 1 Expression in Cholesterol-fed Pigs, Journal of Thoracic and Cardiovascular Surgery, 124(5):950-956, Nov. 2002.

Angelini, G.D., et al., External Stenting Reduces Early Medial and Neointimal Thickening in a Pig Model of Arteriovenous Bypass Grafting, J. Thoracic Cardiovascular Surgery, 112(1):79-84, Jul. 1996.

Angelini, G.D., et al., Towards the Treatment of Saphenous Vein Bypass Graft Failure—a Perspective of the Bristol Heart Institute, Biorheology, 39(3-4):491-499, 2002.

Bambang, L.S., et al., External Biodegradable Supporting Conduit Protects Endothelium in Vein Graft in Arterial Interposition, International Journal of Artificial Organs, 20(7):397-406, 1997.

Barnes, R.W., et al., Mesoaortic Compression of the Left Renal Vein (the so called Nutcracker Syndrome): Repair by a New Stenting Procedure, J. Vascular Surgery, 8(4):415-421, Oct. 1988.

Barra, J.A., et al., Constrictive Perivenous Mesh Prosthesis for Preservation of Vein Integrity, J. Thoracic Cardiovascular Surgery, 92:330-336, 1986.

Batelller, J., et al., Protection from Atherosclerosis in Vein Grafts by a Rigid External Support, Arteriosclerosis and Thrombosis, 13(3):379-384, Mar. 1993.

Beattie, D.K., et al., The Effects of Potassium Channel Openers on Saphenous Vein Exposed to Arterial Flow, Eur. J. Vascular Endovasc. Surg., 15(3):244-249, 1998.

Berkowitz H.D., et al., Renovascular Hypertension in Children: Surgical Repair with Special Reference to the Use of Reinforced Vein Grafts., J. Vasc. Surg., 9(1):46-55, Jan. 1989.

Bourassa, M.G., Long-term Vein Graft Patency, Current Opinion in Cardiology, 9(6):685-691, 1994.

Cagglati, A., et al., The Long Saphenous Vein Compartment, Phlebology, 12:107-111, 1997.

Campeau, L., et al., Atherosclerosis and Late Closure of Aortocoronary Saphenous Vein Grafts: Sequential Angiographic Studies at 2 weeks, 1 year, 5 to 7 years, and 10 to 12 years after Surgery, Circulation, 68(Supp. II):1-7, Sep. 1983.

Dashwood, M.R., et al., Nitric Oxide (NO) Release and NO Synthase in Porcine Venous-Arterial Grafts: Effect of External Stenting, Journal of Molecular and Cellular Cardiology, 29(6):A214 Abstract 237, 1997.

Dashwood, M.R., et al., Does External Stenting Reduce Porcine Vein-Graft Occlusion via an Action on Vascular Nerves?, Journal Cardiac Surgery, 17(6):556-560, 2002.

Deng, X., et al., Efficiency of an External Support to Reduce Lipid Infiltration into Venous Grafts: In Vitro Evaluation, Artificial Organs, 20(11):1208-1214, 1996.

Deng, X., et al., Alternative Blood Conduits: Assessment of Whether the Porosity of Synthetic Prostheses is the Key to Long-term Biofunctionality, Medical & Biological Engineering & Computing, 38(2):219-225, 2000.

Dobrin, P.B., et al., Mechanical and Histologic Changes in Canine Vein Grafts, J. Surg. Res., 44(3):259-265, 1988.

Ferko, A., et al., Autologous Vein Stent-Graft: Feasibility Study, Journal of Vascular and Interventional Radiology, 11(1):111-114, Jan. 2000.

George, S.J., et al., Macro-Porosity is Necessary for the Reduction of Neointimal and Medial Thickening by External Stenting of Porcine Saphenous Vein Bypass Grafts, Atherosclerosis 155(2):329-336, 2001.

George, S.J., et al., An Essential Role for Platelet-Derived Growth Factor in Neointima Formation in Human Saphenous Vein In Vitro, Atherosclerosis, 120:227-240, 1996.

Golledge, J., et al., Circumferential Deformation and Shear Stress Induce Differential Responses in Saphenous Vein Endothelium Exposed to Arterial Flow, J. Clin. Invest., 99(11):2719-2726, Jun. 1997.

Golledge, J., et al., Development of an In Vitro Model to Study the Response of Saphenous Vein Endothelium to Pulsatile Arterial Flow and Circumferential Deformation, Eur. J. Vascular Endovascular Surgery, 13:605-612, 1997.

Grega, G.J., et al., Effects of Dopamine (DA) and SKF-82526, a Selective DA1 Receptor Agonist on Vascular Resistances in the Canine Forelimb, Journal of Pharmacology and Experimental Therapeutics, 22(3):756-762, 1984.

Guldner, N.W., et al., Fluid Dynamics of Autologous Vein Segment Valves With and Without Cylindric External Stents, International J. Artificial Organs, 26(7):659 Abstract P152, 2003.

Hodgson, D.E., et al., Shape Memory Alloys, Metals Handbook (10th Ed.), 2:897-902, 1990.

Hofer, M., et al., Numerical Study of Wall Mechanics and Fluid Dynamics in End-to-Side Anastomoses and Correlation to Intimal Hyperplasia, Journal Biomechanics, 29(10):1297-1308, 1996.

Holzapfel, G.A., et al., A Constitutive Framework for the Inelastic Mechanical Behavior of Arteries, Proceedings of 2001 ASME International Mechanical Engineerng Congress and Exposition, Bioengineering Division (BED), 51:235-236, 2001.

Huynh, Tam T.T., et al., External Support Modulates G Protein Expression and Receptor Coupling in Experimenal Vein Grafts, Surgery, 126(2):127-134, 1999.

Huynh, Tam T.T., et al., Alterations in Wall Tension and Shear Stress Modulate Tyrosine Kinase Signaling and Wall Remodeling in Experimental Vein Grafts, Journal Vascular Surgery, 29(2):334-344, 1999.

Izzat, M.B., et al., Influence of External Stent Size on Early Medial and Neointimal Thickening in a Pig Model of Saphenous Vein Bypass Grafting, Circulation, 94(7):1741-1745,1996.

Jeremy, J.Y., et al., The Influence of External Stent Porosity on Early Neointima Formation and Medial Wall Thickening in a Pig Model of Saphenous Vein Bypass Grafting, European Heart Journal, 20:274 Abstract P1533, Aug. 1999.

Jeremy, J.Y., et al., Nitric Oxide, Prostacyclin and Cyclic Nucleotide Formation in Externally Stented Porcine Vein Grafts, Atherosclerosis 141(2):297-305, 1998.

Jeremy, J.Y., et al., A Bioabsorbable (Polyglactin), Nonrestrictive, External Sheath Inhibits Porcine Saphenous Vein Graft Thickening, Journal of Thoracic and Cardiovascular Surgery, 127(6):1766-1772, Jun. 2004.

Karayannacos, P.E., et al., Potential Role of Velocity and Wall Tension in Vein Graft Failure, J. Cardiovascular Surgery, 21:171-178, 1980.

Klimek, W., et al., In Vitro Intravascular Ultrasound Imaging of Biocompound Vein Grafts: Comparison to Histology, European Heart Journal, 20:405 Abstract P2142, Aug. 1999.

Kohler, T., et al., The Effect of Rigid External Support on Vein Graft Adaptation to the Arterial Circulation, J.. Vasc. Surg., 9(2):277-285, 1989.

Krejca, M., et al., Effects of External Stenting on the Durability of Vein Grafts, Kardiologia Polska, 57(8):125-130, 2002.

Kus, H., Przeszczepy Zylne Wzmocnione Porowat A Oslon A Pollestrow A, Polski Tygodnik Lekarski, 19:704-706, 1964 (English Language Title only).

Lardenoye, J.H.P., et al., Inhibition of Accelerated Atherosclerosis in Vein Grafts by Placement of External Stent in ApoE*3-Leiden Transgenic Mice, Arteriosclerosis Thromb. Vasc. Biol., 22(9):1433-1438, 2002.

Lendlein, A., et al., AB-Polymer Networks Based on Oligo (caprolactone) Segments Showing Shape-Memory Properties, Proc. Natl. Academy Sci., 98(3):842-847, 2001.

Liu, S. Q., et al., A Possible Role of Initial Cell Death Due to Mechanical Stretch in the Regulation of Subsequent Cell Proliferation in Experimental Vein Grafts, Biomechan. Model Mechanobiol., 1:17-27, 2002.

Liu, S.Q., et al., Partial Prevention of Monocyte and Granulocyte Activation in Experimental Vein Grafts by Using a Biomechanical Engineering Approach, Journal of Biomechanics, 32(11):1165-1175,1999.

Liu, S.Q., et al., Prevention of Mechanical Stretch-Induced Endothelial and Smooth Muscle Cell Injury in Experimental Vein Grafts, Journal of Biomechanical Engineering, 122(1):31-38, Feb. 2000.

McGregor, E., et al., Circumferential Stretching of Saphenous Vein Smooth Muscle Enhances Vasoconstrictor Responses by Rho Kinase-Dependent Pathways, Cardiovascular Research, 53(1):219-226, 2002.

Meguro, T., et al., Effect of External Stenting and Systemic Hypertension on Intimal Hyperplasia in Rat Vein Grafts, Neurosurgery, 46(4):963-970, Apr. 2000.

Mehta, D., et al., External Stenting Reduces Long-term Medial and Neointimal Thickening and Platelet Derived Growth Factor Expression in a Pig Model of Arteriovenous Bypass Grafting, Nature Medicine, 4(2):235-239, Feb. 1998.

Mehta, D., et al., Prostacyclin, Nitric Oxide and Cyclic Nucleotide Synthesis in Stented and Unstented Porcine Vein Grafts, British Journal of Pharmacology, 119:Abstract 132P, 1996.

Moritz, A., el al., Use of Varicose Veins as Arterial Bypass Grafts, Cardiovasc. Surg., 1(5):508-512, 1993.

Moritz, A., et al., A Method for Constricting Large Veins for use in Arterial Vascular Reconstruction, Artificial Organs, 14(5):394-398,1990.

Moritz, A., et al., The Use of Mesh-Tube-Constricted Dilated or Varicose Veins as Arterial Bypass Conduit, Thorac. Cardiovasc. Surg., 40(6):356-360, 1992.

Moritz, A., et al., Mesh Constricted Varicose and Dilated Veins Used as Arterial Bypass Grafts, International Journal Artificial Organs, 14(7):435-440, 1991.

Moritz, A., et al., Mesh Tube-Calibrated Varicose Veins for Coronary Artery Bypass Grafting, Ann. Thorac. Surg., 57:240-242, 1994.

Moritz, A., et al., Mesh Tube-Constricted Varicose Veins used as Bypass Grafts for Infrainguinal Arterial Reconstruction, Arch. Surg., 127(4):416-420,1992.

Moritz, A., et al., Ummantelte Dilatierte oder Varikose Venen als Arterielles Bypasstransplantat: Experimentelle und Erste Klinische Ergebnisse, Vasa, 20(3):222-229, 1991 (English Language Summary on p. 228).

Neufang, A., et al., External Reinforcement of Varicose Veins with PTFE Prosthesis in Infrainguinal Bypass Surgery, Thoracic Cardiovascular Surgery, 51(2):62-66, 2003.

Panneton, J.M., et al., Superior Vena Cava Syndrome: Relief with a Modified Saphenojugular Bypass Graft, Journal Vascular Surgery, 34(2):360-363, 2001.

Papadopoulos, N.J., et al., A Fascial Canal for the Great Saphenous Vein: Gross and Microanatomical Observations, Journal of Anatomy, 132(3):321-329, May 1981.

Pillet, J., Our Clinical Experience with Reinforcement of Free Autogenic Venous Grafts by Inert Prosthesis in Reparation of Loss of Arterial Substance. Application of the Procedure to Treatment of Aneurysmal Dilatation of a Femoral Venous Graft, Memoires, Adademie de Chirurgie, 95(1):64-67, 1969 (English Language Abstract only).

Powell, J.T., et al., Molecular and Cellular Changes in Vein Grafts: Influence of Pulsatile Stretch, Current Opinion in Cardiology, 13(6):453-458, 1998.

Pshenisnov, K.P., et al., Comparative Analysis of Structural Change in a Free Autovenous Graft and in a Transplant with Spiral Reinforcement after Correction of Experimental Arterial Defects, Cor Vasa, 30(3):218-224, 1988.

Shimizu, K., et al., Shape Memory Effect: Mechanism, Shape Memory Alloys, (Funakubo, H., Ed.), Gordon and Breach Science (Pub.), 1:1-60, 1987.

Shore, J.M., et al., A Comparative Study of Canine Venous Autografts, Journal of Cardiovascular Surgery, 17:67-75, 1964.

Soury, P., et al., Prosthetic Reinforcement of Varicose Saphenous Vein Grafts for Infrainguinal Bypass, Ann. Vascular Surgery, 13(3):290-293, 1999.

Sparks, C.H., et al., Carotid Artery Replacement with Reinforced Autogenous Vein Grafts, Angiology 14:541-551, Nov. 1963.

Stooker, W., et al., Perivenous Support Reduces Early Changes in Human Vein Grafts: Studies in Whole Blood Perfused Human Vein Segments, J. Thoracic Cardiovascular Surg., 121(2):290-297, 2001.

Stooker, W., et al., Surgical Sealant in the Prevention of Early Vein Graft Injury in an Ex Vivo Model, Cardiovascular Pathology, 12(4):202-206, 2003.

Stooker, W., et al., Perivenous Application of Fibrin Glue Reduces Early Injury to the Human Saphenous Vein Graft Wall in an Ex Vivo Model, European Journal of Cardio-thoracic Surgery, 21(2):212-217, 2002.

Stooker, W., et al., Pressure-Diameter Relationship in the Human Greater Saphenous Vein, Ann. Thoracic Surg., 76(5):1533-1538, 2003.

Tanabe, T., et al., Wall Reinforcement with Highly Porous Dacron Mesh in Aortic Surgery, Ann. Surg., 191(4):452-455, 1980.

Tedgul, A., et al., External Stenting & Atherosclerosis, Nature Medicine, 4(6):645, Jun. 1998.

Trubel, W., et al., Compliance Mismatch and Formation of Distal Anastomotic Intimal Hyperplasia in Externally Stiffened and Lumen Adapted Venous Grafts, Eur. J. Vasc. Endovasc. Surg., 10(4):415-423, 1995.

Trubel, W., et al., Compliance and Formation of Distal Anastomotic Intimal Hyperplasia in Dacron Mesh Tube Constricted Veins used as Arterial Bpass Grafts, ASAIO Journal, 40(3):M273-278, 1994.

Vijayan, V., et al., External Supports and the Prevention of Neointima Formation in Vein Grafts, European Journal Vascular Endovascular Surg., 24(1):13-22, 2002.

Vijayan, V., et al., Long-term Reduction of Medial and Intimal Thickening in Porcine Saphenous Vein Grafts with a Polyglactin Biodegradable External Sheath, Journal Vascular Surgery, 40(5):1011-1019, 2004.

Yang, B., et al., Effect of the Biodegradable Chitosan External Stent on the Early Changes in the Rabbit Vein Grafts, Chinese Journal of Surgery, 41(9):688-690, Sep. 2003 (English Language Abstract).

Zhao, L., et al., Results of Autogenous Vein Grafts in Repair of Major Arterial Injuries to the Upper and Lower Extremities with Reference to Wall Shear Stress, International Journal of Angiology, 6(2):99-103, 1997.

Zidi, M., et al., Mechanical Analysis of a Prototype of Small Diameter Vascular Prosthesis: Numerical Simulations, Computers in Biology and Medicine, 33:65-75, 2003.

Zurbrugg, H.R., et al., The Biocompound Method in Coronary Artery Bypass Operations: Surgical Technique and 3-year Patency, Ann. Thorac. Surg., 70:1536-1540, 2000.

Zurbrugg, H.R., et al., Prevention of Venous Graft Sclerosis with Clopidogrel and Aspirin Combined with a Mesh Tubing in a Dog Model of Arteriovenous Bypass Grafting, European Journal Vascular Endovascular Surgery, 22(4):337-341, 2001.

Zurbrugg, H.R., et al., Reduction of Intimal and Medial Thickening in Sheathed Vein Grafts, Ann. Thorac. Surg., 68(1):79-83, 1999.

Zurbrugg, H.R., et al., The use of Biocompound-Grafts Together with Varicose Veins, Journal Cardiovascular Surgery, 37 (Suppl. 1 to No. 6):143-146, 1996.

Zurbrugg, H.R., et al., Improvement of the Flow Profile in Bypass Surgery: First Clinical Experience with the Ultraflexible Biocompound-Graft, Swiss Surgery, Suppl. 1:8-12, 1996 (English Language Abstract on p. 9).

Zwolak, R.M., et al., Kinetics of Vein Craft Hyperplasia: Association with Tangential Stress, J. Vasc. Surg. 5(1):126-136, 1987.

* cited by examiner

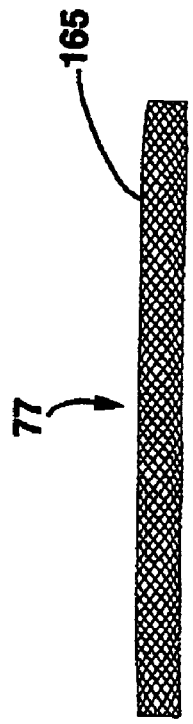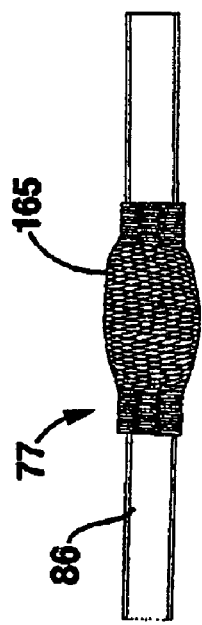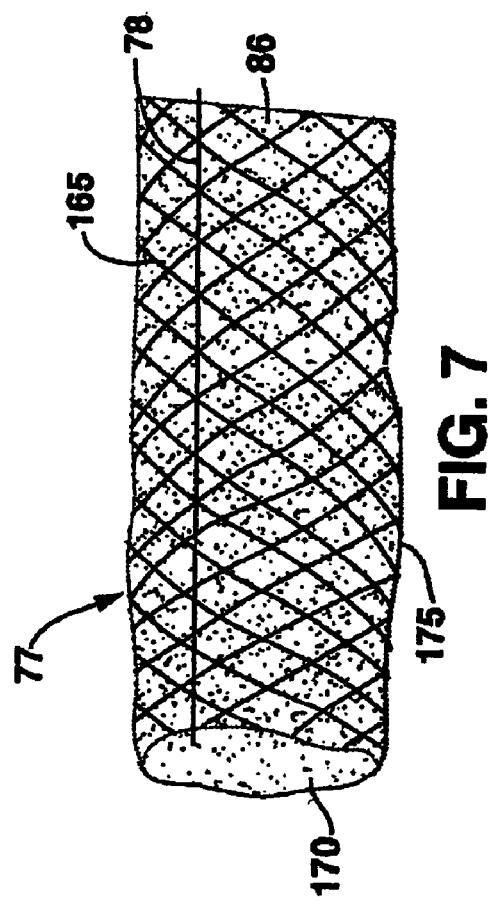

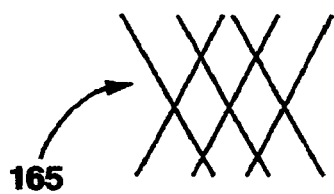
FIG. 8
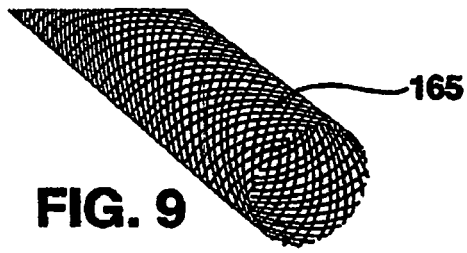
FIG. 9
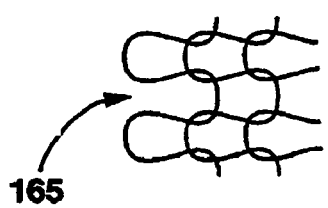
FIG. 10
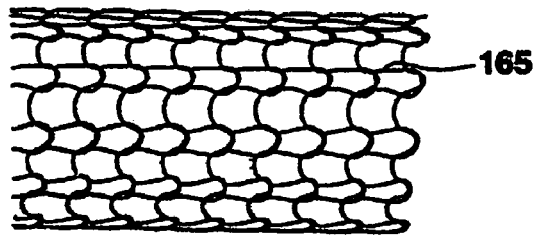
FIG. 11
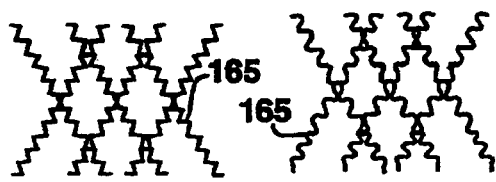
FIG. 12  FIG. 14
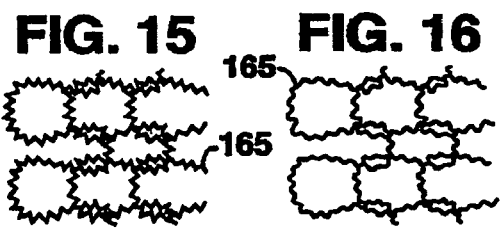
FIG. 15  FIG. 16
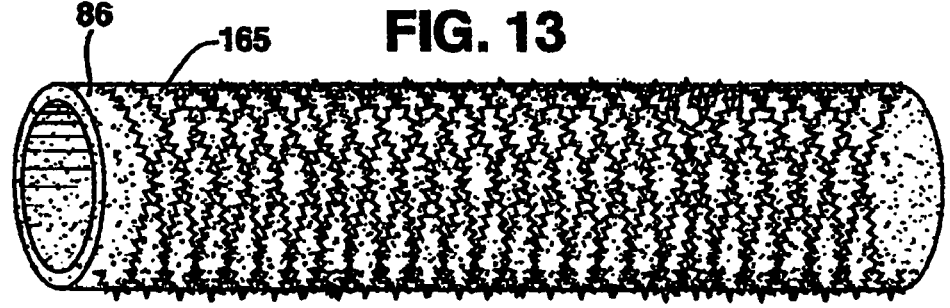
FIG. 13

COMPLIANT VENOUS GRAFT

CROSS REFERENCE

This application claims priority to U.S. Provisional Application Ser. No. 60/466,226 titled "Compliant Venous Stent" filed on Apr. 28, 2003, incorporated herein by reference.

FIELD OF THE INVENTION

This invention involves a venous graft involving a vein segment and a supportive sheath chosen to provide the graft with mechanical compliance properties which resemble those of a healthy native artery.

BACKGROUND OF THE INVENTION

Various types of vascular prostheses are known or available. Commercially available synthetic vascular grafts in use are commonly made from expanded polytetrafluoroethylene (e-PTFE), or woven, knitted, or velour design polyethylene terephthalate (PET) or DACRON®. These prosthetic vascular grafts may have various drawbacks. When used for repairing or replacing smaller diameter arteries, these grafts may fail due to occlusion by thrombosis or kinking, or due to an anastomotic or neointimal hyperplasia (exuberant cell growth at the interface between artery and graft). Another problem may involve expansion and contraction mismatches between the host artery and the synthetic vascular prosthesis, which may result in anastomotic rupture, stimulated exuberant cell responses, and disturbed flow patterns and increased stresses leading to graft failure.

Problems also exist with the use of autologous saphenous vein grafts in these applications. Use of autologous saphenous vein grafts to bypass blockages in coronary arteries has become a well-established procedure. However, their success in the long term has been limited. In the coronary position, the literature reports a low (45-63%) patency of vein grafts after 10-12 years. It is believed that these failures result from remodeling of the implanted vein in response to greatly increased internal pressure, that is, as the vein is required to function as an artery. In general, arteries have substantial musculature and, although able to expand diametrically in response to increased internal pressure, are capable of withstanding normal arterial pressure variances. Veins, on the other hand, are not required to withstand arterial pressure variances and are relatively incapable of withstanding the higher arterial pressures without substantial bulging. In this regard, the nominal venous diameter seen under nominal venous pressure is seen to approximately double upon exposure to arterial pressure.

Increases in lumenal diameter of these magnitudes in vein segment implants are accompanied by increases in tangential stress. Tangential stress has been shown to be proportional to the lumenal radius-wall thickness ratio. In healthy arteries, this ratio remains constant across multiple species. However, this does not occur in veins. It is believed that a vein's smooth muscle cells increase their growth rate and secrete extracellular matrix components in response to such increases in tangential stress. This becomes a remodeling response, and is likely an attempt by the vein to reduce the lumenal radius-wall thickness ratio, and consequently the tangential stress. However, it appears that these reactions overcompensate in the veins, resulting in the phenomenon of neointimal hyperplasia yielding grossly thickened and stiff graft walls. As the dilation of the vein segment continues, the resulting mismatch between the vein and artery diameters may lead to disturbance of flow patterns, which may also favor the formation of thrombi.

A venous graft that reduces or eliminates such failings in the prior art is required.

SUMMARY OF THE INVENTION

It has now been found that a vein segment, if externally supported by an appropriate, flexible, radially-resiliently tubular support, can function, in much the same fashion as the artery to be replaced. That is, it functions without undue bulging or aggravated mismatching phenomena leading to graft failure. Unless otherwise indicated, the term "compliance" means the ratio of the diameter change of a vessel as it expands in the radial direction in response to a given change in vessel pressure, and the values for compliance referred to below result from dynamic, in vitro testing. As described in greater detail below, the compliance of venous graft is largely dependent upon the compliance of the external, radially resilient support.

The invention in one embodiment, accordingly, relates to a flexible, resilient, generally tubular external support within which may be supported a vein segment to form a venous graft. The tubular support is capable of resilient radial expansion in a manner mimicking the compliance properties of an artery, and compliance figures in the range of 3 to 30%/100 mm Hg are appropriate. The tubular support may be formed of a knitted or woven fiber mesh that is so formed as to exhibit the needed compliance properties.

The invention in certain embodiments provides a venous graft for replacement of a section of an artery. The graft comprises a flexible, resilient, generally tubular external support and a vein segment carried within and having an ablumenal surface in contact with and supported by the tubular support, the venous graft being capable of resilient radial expansion in a manner mimicking the compliance properties of an artery. Compliance figures in the range of 3 to 30%/100 mm Hg are appropriate. The tubular support may take the form of a fiber mesh, such as a knitted, braided or woven mesh, the fibers of which may, if desired, be appropriately crimped to provide the required resiliency and compliance.

In other embodiments, the invention relates to a method for producing a venous graft for use in replacing a section of an artery. A segment of a vein is provided, and is sheathed in a generally tubular support in supportive contact with the ablumenal surface of the vein segment. The support is sufficiently flexible and radially resilient as to provide the resulting graft with compliance properties mimicking the compliance properties of an artery. Sheathing of the vein segment within the tubular support may be accomplished by supporting the generally tubular support upon an exterior surface of an applicator having an internal passage within which is positioned the vein segment, and removing the applicator to permit the tubular support to come into supportive contact with the ablumenal surface of the vein segment. Axial dimensional changes in the tubular support may be controlled as necessary to provide the venous graft with the desired compliance properties mimicking arterial compliance properties.

Other embodiments of the invention relate to venous grafts that include a flexible, resilient, generally tubular external support formed of a shape memory alloy, and a vein segment carried within and having an ablumenal surface in contact with and supported by the tubular support. The shape memory support may be placed around a vein segment when the shape memory material is in a first enlarged configuration. The tubular support comes into supportive contact with the ablumenal surface of the vein when the support is transformed, as by a temperature increase, into a second configuration different from the first configuration. The shape memory support in its second configuration may exhibit superelastic properties and in any event is sufficiently flexible and resilient as to provide the venous graft with compliance properties mimicking the compliance properties of an artery. Compliance figures in the range of 3 to 30%/100 mm Hg are appropriate. The tubular support may take the form of a wire mesh made of shape memory alloy, such as a knitted or woven mesh, the wires of which may, if desired, be appropriately crimped to provide the required resiliency and compliance.

BRIEF DESCRIPTION OF THE DRAWING

FIG. 5 is a photograph of a tubular support in a first configuration, shown in an axially compressed and radially expanded configuration and supported on a plastic tube;

FIG. 6 is a photograph of the tubular support of FIG. 5 in an axially elongated and radially reduced configuration to conform to a vein outer diameter;

FIG. 7 is a side view of the graft of FIG. 6, showing a length-governing element;

FIG. 8 is a schematic view of braided elements;

FIG. 9 is a perspective view of a braided tubular support;

FIG. 10 is a schematic view of knitted elements;

FIG. 11 is a side view of a section of a knitted tubular support;

FIG. 12 is a view of angular pre-braiding crimped elements;

FIG. 13 is a perspective, schematic view of an angular pre-braiding crimped tubular support;

FIG. 14 is a view of rounded pre-braiding crimped elements;

FIG. 15 is a view of angular pre-knitting crimped elements;

FIG. 16 is a view of rounded pre-knitting crimped elements;

DETAILED DESCRIPTION OF THE PRESENTLY PREFERRED EMBODIMENTS

Applicants have recognized that significant deficiencies attend to the past methodologies and devices relating to the increased pressures experienced by vein grafts utilized in arterial positions. The increased pressures lead to excessive dilation of vein grafts in arterial circulation, leading to the development of intimal hyperplasia, which causes occlusion of the vessel.

Intimal hyperplasia is believed to be a primary reason for vein graft failure. In this context it is known that intact endothelium acts in a manner to protect against the proliferation of underlying vascular smooth muscle cells, known as VSMC. The intact endothelium also plays a role in VSMC contractile responses. The VSMC have also been shown to release factors with long term physiological effects on the endothelial cells, including maintenance of a non-proliferative state. By comparison, the pathogenesis of intimal hyperplasia in a vein graft may follow the sequence of dilatation under arterial pressure; overstretching to maximum capacity; disruption of borders of endothelial cells; rupture of internal elastic membranes; migration of smooth muscle cells into the intimal layer and resultant unbalanced proliferation; atrophy of media and further consolidation of stiffness; and graft arteriosclerosis with traumatic media necrosis and atrophy, as well as pathological surface and wall stress and strain. These phenomena may result in a decrease in vein graft patency within six years. Intimal hyperplasia may be observed in such grafts from about 16 months, while anastomotic intimal hyperplasia may occur at about 18 months, and arteriosclerosis may occur from about 45 months.

Figure 1:
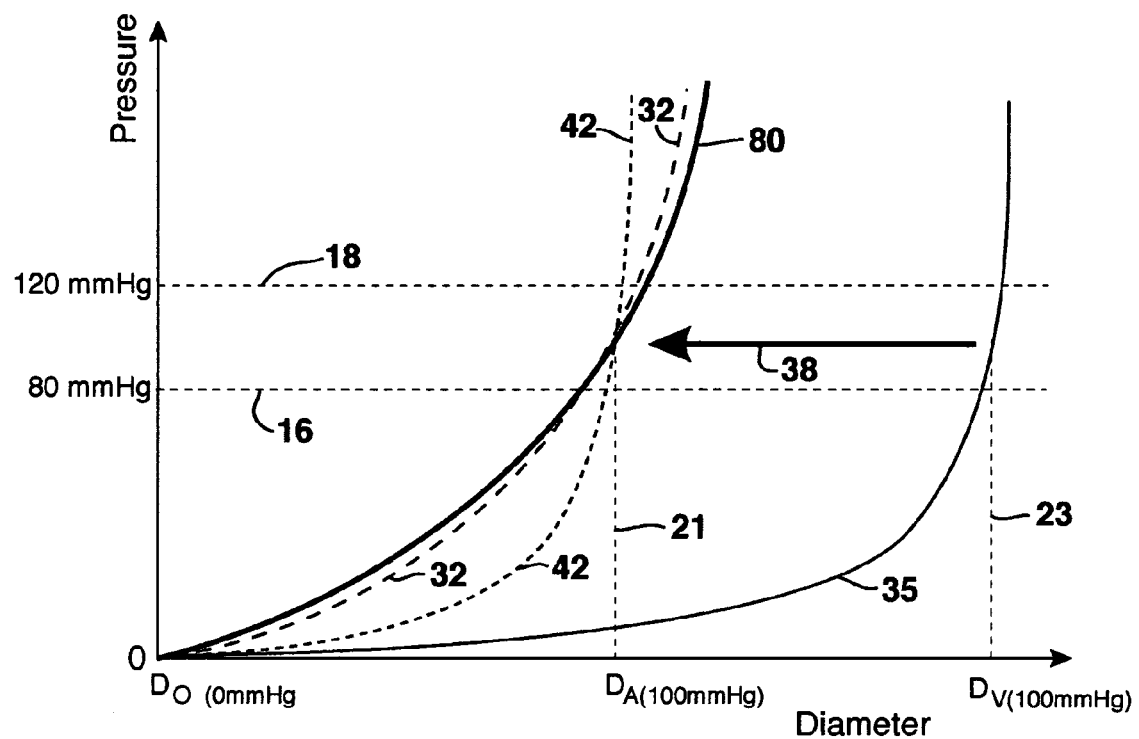
FIG. 1 is a pressure versus diameter graph typifying the characteristics of a native vein, native artery, a non-compliant stented vein, and a compliant stented vein.

Others have attempted to overcome certain of these problems by use of metallic or polymeric external structures designed to arrest the dilation of the vein graft. FIG. 1 graphs blood pressure against vessel diameter, with $D_0$ representing the vessel diameter at zero pressure. As shown in this graph, lines 16, 18 represent the normal diastolic, i.e. low (80 mm Hg) and normal systolic, i.e. high (120 mm Hg) physiological blood pressure range for humans. Point 21 may represent the diameter of an artery ($D_A$) at 100 mmHg, and point 23 may represent the diameter of a vein ($D_V$) at the same pressure of 100 mmHg. An unstented native artery reacts to pressure loading as shown at line 32, and an unstented vein reacts to the same loading as shown at line 35. The use of known stents with vein grafts results in movement of line 35 in the direction shown by arrow 38, resulting in the approximate profile indicated at line 42 showing the response of a pressure loaded vein and non-compliant stent combination. Although this prevents over-dilation, and some advantage accrues, this may lead to further unhealthy sequelae. Also, to the extent that vein-stent combination devices may be shown to limit some of the dilation and intimal hyperplasia in the mid-graft region, they may not be able to prevent intimal hyperplasia at the anastomoses. This can be a significant problem for vein grafts that are transplanted into the arterial circulation vasculature. Prior attempts to resolve these problems fail to recognize the full implications of a vein being used in these situations. Accordingly, factors in the design of a vein-graft that may have a significant impact on its long term patency may have been missed.

One important factor in proper remodeling is that of proper cyclic stretch. Applicants are able to incorporate this concept into vein-stent grafts of the invention. In similar manner, the role of vascular endothelial growth factor (VEGF) in vascular smooth muscle cells may be very important to the design of a preferred arterial vein-stent graft. It is known that low concentrations of VEGF may play a role in preserving and repairing the arterial lumenal endothelial layer. Further, it is suggested that activation of the VEGF receptor KDR is affected by cyclic stretch. Applicants believe that the phenomenon of upregulation of VEGF expression by physiological stretching of vascular smooth muscle cells is one reason for redesigning a vein-stent graft which has improved, controllable cyclic stretch features.

A further consideration is the influence of tensile stress/strain on the structure and organization of smooth muscle cells during development and remodeling, particularly as to the orientation of such cells. In a larger topographical sense, this may also relate to the role of blood flow in the formation of focal intimal hyperplasia in known vein grafts, including inducement of eddy blood flow at locations of graft-host diameter mismatch.

These considerations and deficiencies can be addressed with the various structures and methodologies of the present invention in which a vein graft is provided that exhibits compliance properties mimicking those of healthy arteries. Radial expansion and contraction of the graft is permitted in a manner that mimics the radial expansion and contraction of an artery to at least closely approach the desired result in which the vein graft, its connections to adjacent arterial ends or stumps, and the adjacent arterial portions tend to expand and contract in a similar manner, to thereby substantially avoid anastomotic compliance mismatches. This is accomplished through the use of a flexible, resilient, generally tubular external support that engages the ablumenal surface of a vein segment carried within the support, the support being so fabricated as to functionally provide the graft with the compliance properties of an artery.

Compliance Properties

As noted earlier, compliance is the ratio of the diameter change of a vessel in the radial direction to a given change in vessel pressure, and the values for compliance referred to below result from dynamic, in vitro testing. Compliance values are reported here as percentage changes in the internal diameter of a vessel per a 100 mm Hg change in vessel pressure, as measured in the range of normal blood pressures, that is, from about 80 mm Hg to about 120 mm Hg. In the laboratory, it is convenient to measure compliance through the use of an elongated balloon structure over which a candidate tubular support is positioned. Distilled water at about 37° C. is pumped into the balloon to cause it to inflate, and the pressure within the balloon is cycled between 0 mm Hg and 140 mm Hg at a frequency of about 72 cycles per minute to mimic a normal pulsatile blood flow. The change in internal volume is measured between 0 mm Hg and 140 mm Hg to provide pressure/volume data. From this data is subtracted the pressure/volume data resulting from repeating the procedure with the balloon alone, and from the resulting pressure/volume data the percentage change in the internal diameter of the tubular support between 80 and 120 mm Hg can be calculated. It is convenient to express this radial compliance value as %/100 mm Hg.

Figure 2:
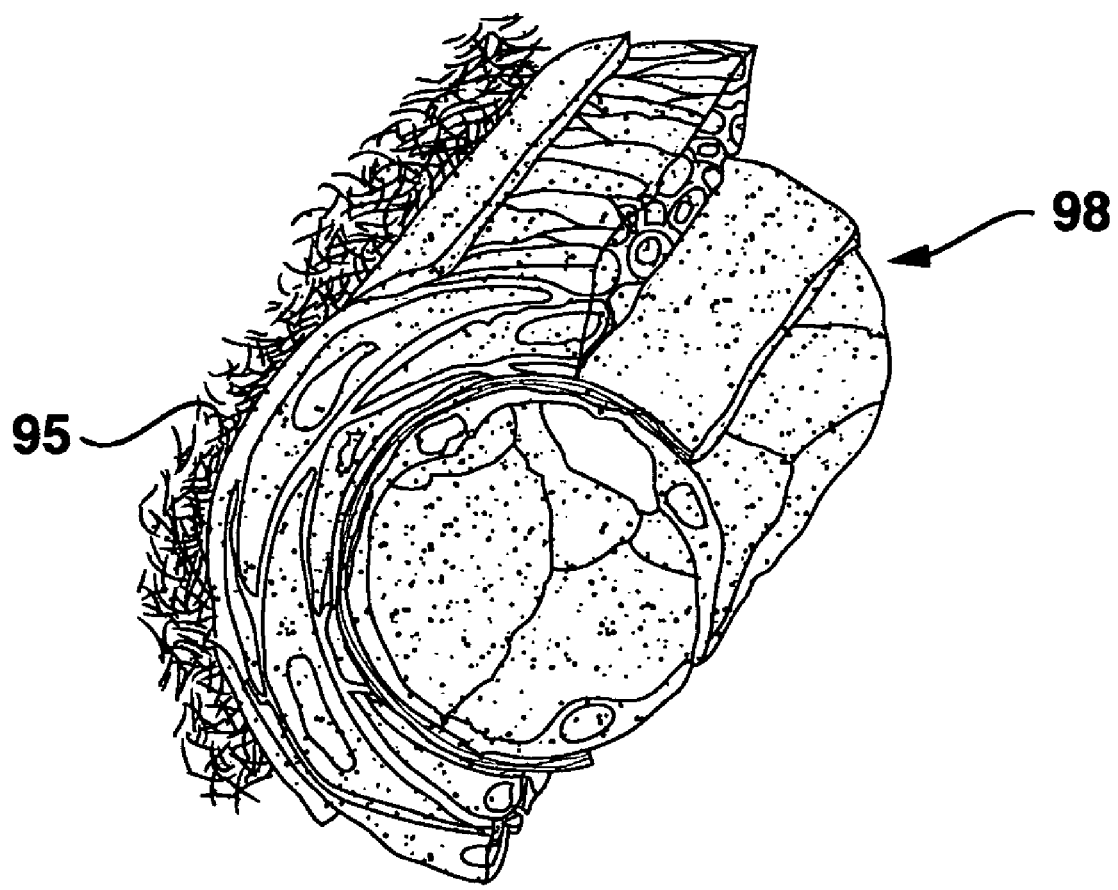
FIG. 2 is a schematic cross-sectional view of an artery.

The compliance of an implanted venous graft may be measured in vivo through the use of ultrasound techniques in which the vein graft is visualized in a cross-sectional view and the dimensional change of the vessel with varying blood pressure is recorded for at least one and usually a number of cardiac cycles. The cross-sectional lumenal area of the vein graft is measured for the smallest cross-sectional configuration and the largest cross-sectional configuration for one cardiac cycle. The smallest cross-sectional configuration of the vein graft lumen is associated with diastolic blood pressure whereas the largest cross-sectional configuration is associated with systolic pressure. The cross-sectional lumenal area values for diastolic and systolic blood pressure are used to calculate the lumenal diameter values and the vein graft compliance. Compliance values of a venous graft measured in vivo often are slightly larger that the compliance values measured in the laboratory, and the compliance values referred to herein are laboratory values resulting from the in vitro measurements described above FIG. 2 is a sectional representation of vascular tissue useful for illustrating the relation of the natural arterial structure with the prosthetic venous graft structure of the invention. The natural adventitial layer 95 of an artery 98 is comprised of two main tissue types that contribute to the mechanical properties of the natural artery, namely elastin and collagen. The mechanical properties of these two soft tissue components are described in Table I below:

TABLE I

| Soft Tissue | Elastic Modulus (Pa) | Max Strain (%) |
| --- | --- | --- |
| Elastin | $4 \times 10^5$ | 130 |
| Collagen | $1 \times 10^9$ | 2-4 |

Figure 3:
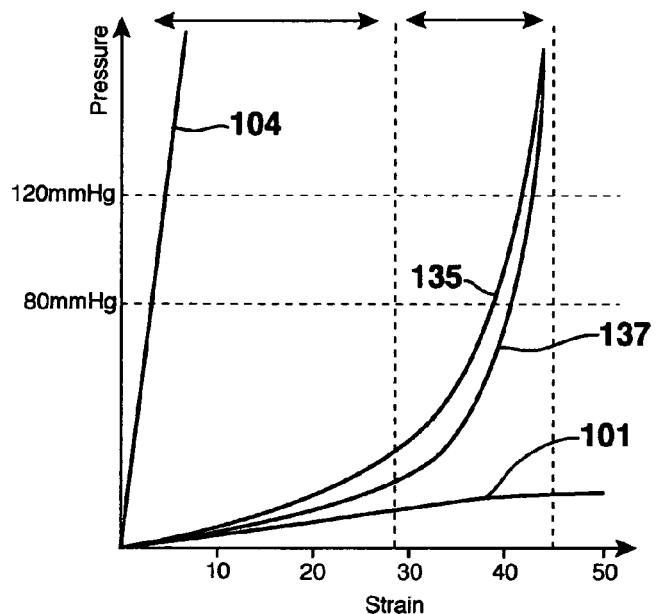
FIG. 3 is a representative pressure versus strain graph.

As shown in the above table, these two soft tissue types have large differences in mechanical properties. Elastin is very elastic, and collagen is very stiff in comparison. These two tissue types are combined in the adventitial layer to produce a non-linear elastic response. As shown in FIG. 3, the combined effect of the characteristics of elastin 101 and collagen 104 (having a greater role at higher strains) results in a non-linear response curve (shown loading at 135 and unloading at 137) within the physiological pressure range of a natural artery between about 80-120 mm Hg. This characteristic of pulsatile expansion and contraction of arteries requires fine mechanical compliance of any prosthetic graft, i.e., a close mimicking by the prosthetic device of the mechanics and timing of the natural artery distending and reshaping under change in blood pressure.

From an engineering standpoint, the following relationships may be helpful from a design standpoint in producing venous stent grafts of the invention.

$$C_d = \frac{\Delta D}{D_{diastolic} \Delta P} \times 100 \times 100 \, mmHg$$

in which $C_d$ is compliance, P is blood pressure, D is vessel diameter, and $\Delta D$ represents the diameter change between systolic and diastolic pressures.

The stiffness of blood vessels is stated as a stiffness index ($\beta$), and is a measure of the changes of curvature and diameter, stated as:

$$\beta = \frac{\ln \frac{P_{systolic}}{P_{diastolic}}}{\frac{\Delta D}{D_{diastolic}}} = D_{diastolic} \frac{\ln P_{systolic} - \ln P_{diastolic}}{\Delta D}$$

A related characteristic of blood vessels is that of elastic modulus (K), which is considered a measure of stiffness, and is stated as:

$$K = \frac{V_{diastolic} \Delta P}{\Delta V} \propto \frac{D_{diastolic} \Delta P}{\Delta D} \propto \frac{1}{C}$$

in which C is compliance. In terms of diametric compliance, as an example, $$K = D_{diastolic} \frac{P_{systolic} - P_{diastolic}}{D_{systolic} - D_{diastolic}} = D_{diastolic} \frac{\Delta P}{\Delta D}$$

Figure 4:
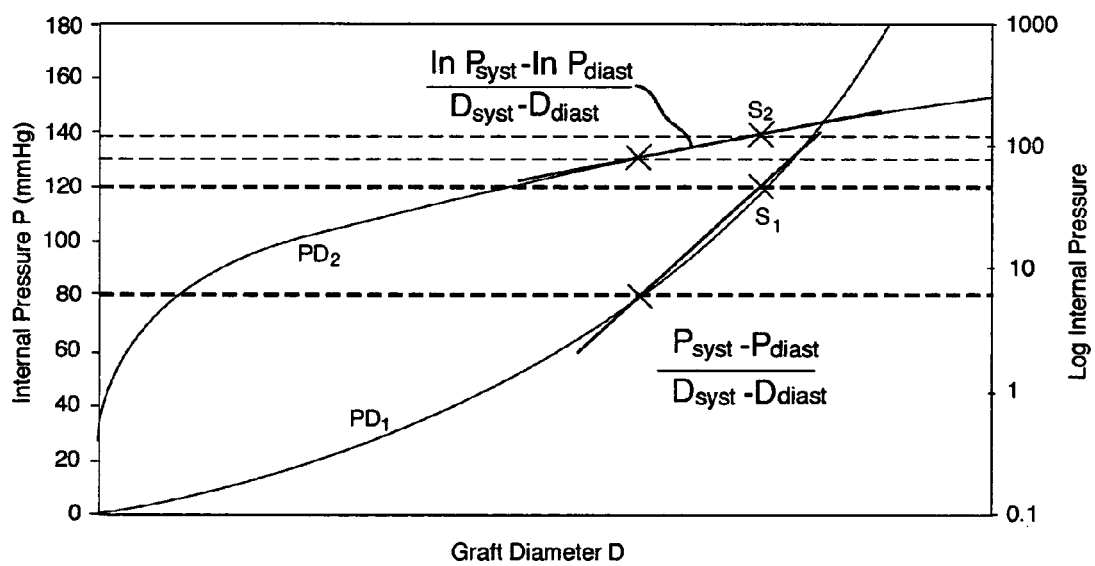
FIG. 4 is a pressure versus graft diameter graph.

FIG. 4 shows that the Elastic Modulus (K), as defined in above equations, is proportional to the secant $S_1$ of the pressure-diameter curve $PD_1$, plotted on a linear scale (left y-axis in FIG. 4), between diastolic and systolic pressure. The slope, $(P_{syst}-P_{diast})/(D_{syst}-D_{diast})$, of the secant $S_1$ is a good approximation to the slope of the pressure-diameter curve $PD_1$ in that pressure range. From the above equations for the Elastic Modulus (K) it can be appreciated that the Elastic Modulus (K) is not equal to the slope of the secant $S_1$ but is proportional to the slope by a factor $D_{diastolic}$. Compliance ($C_d$) is approximately proportional to the Elastic Modulus (K) hence it is approximately proportional to the inverse of the secant $S_1$ of the pressure-diameter curve $PD_1$ between diastolic and systolic blood pressure.

The stiffness index ($\beta$) is proportional to the secant $S_2$ of the pressure-diameter curve $PD_2$ between diastolic and systolic blood pressure when the pressure-diameter curve is plotted on a logarithmic pressure scale (right y-axis in FIG. 4). The slope of the secant $S_2$ is $(\ln P_{syst}-\ln P_{diast})/(D_{syst}-D_{diast})$ and is a good approximation to the slope of the pressure-diameter curve $PD_2$ in that pressure range. It can be again appreciated, from the above equations for the Stiffness Index ($\beta$) that the Stiffness Index ($\beta$) is not equal to the slope of the secant $S_2$ but is proportional to the slope by a factor $D_{diastolic}$.

Compliance data of natural human vessels is categorized by vessel type and by age of the vessel (i.e., age of patient). For example, a common carotid artery has about a 6.6%/100 mm Hg compliance value. The values for a superficial femoral artery and a femoral artery are 6-10%/100 mm Hg. A value for a saphenous vein, however, is about 4.4%/100 mm Hg, while an aorta ranges generally from about 20-50%/100 mm Hg, depending on the location. Also, the lengths of grafts according to location in the body must be considered, and substantial lengthwise variance in graft lengths is not uncommon. It is also known that the diameter of various arteries change over time, and this may have a significant impact on overall compliance values. Returning to FIG. 1, line 80 represents the pressure-diameter data that certain embodiments of venous grafts of the invention seek to emulate, wherein the compliance properties of a native artery (line 32) is closely mimicked.

Support Materials and Manufacture

The radially resilient support may be manufactured from any biologically acceptable material that possesses the ability to be shaped into a tubular structure having the required compliance. Polymeric fibers may be employed, such as polyurethanes, polyethylene terephthalate, polypropylene, and polytetraflouroethylene, and good results may be obtained through the use of wires of such metals as stainless steel and cobalt-chromium alloys. Wires made of shape memory alloys such as nitinol may be used to advantage. Shape memory elements or filaments may be made of one or more shape memory materials as exemplified in the following table, it being understood that this is not to be considered an exhaustive list. Also, any metal or metal alloy may be coated with a polymer for improved biocompatibility, recognizing that the polymer may or may not be biodegradable.

| ALLOYS | POLYMERS |
| --- | --- |
| Ag—Cd | Two component system based on oligo(Σ-caprolactone)dimethacrylate and N-butyl acrylate |
| Au—Cd | Polyurethanes |
| Cu—Al—Ni | Polynorborenes |
| Cu—Sn | Poly(ether ester)s consisting of poly(ethylene oxide) and poly(ethylene terephthalate) (EOET copolymers) |
| Cu—Zn | Ethylene vinyl acetate copolymers |
| Cu—Zn—Si | Polystyrene polybutadiene copolymer |

-continued

| ALLOYS | POLYMERS |
| --- | --- |
| Cu—Zn—Sn | |
| Cu—Zn—Al | |
| In—Ti | |
| Ni—Al | |
| Ni—Ti | |
| Fe—Pt | |
| Mn—Cu | |
| Fe—Mn—Si | |

With respect to shape memory alloys, other design considerations include temperatures, different diameters and radial compliance, shape transformation dimensional changes, and wire thicknesses. Generally, shape memory alloys and shape memory polymers may have transformation temperatures which are below physiological temperatures, i.e., 37° C., to ensure self-righting responses. Preferably, transformation temperatures will also be above room temperature to ensure that the shape memory material reinforcing does not need to be refrigerated for storage purposes. Thus, the ideal shape memory transformation temperatures will likely be between 21° and 37° C. This transition may either be a two-way or a one-way directional transition, with a currently preferred embodiment including a two-way directional transition. The transition temperature range can either be a short, i.e. 0.5° C., or a long transition temperature range, i.e. 10° C., where the shape is proportionally regained over this temperature range. For example, for a desired temperature transition to be 100% complete at 25° C. but with it starting at 20° C., then this would yield a temperature range of 5° C. The changes in radial diameter due to the shape memory material experiencing transformation dimensional changes is preferably in a range of from 5% to 30%.

An embodiment of a tubular support utilizing a shape memory alloy is illustrated in FIGS. 5 and 6. FIG. 5 shows an arterial reinforcement tubular support 77 formed of one or more shape memory material elements 165. These elements are braided, but may also be knitted, into a generally tubular structure designed for placement around a portion of a vein to produce an arterial graft. In this example, a shape memory alloy is employed because of its so-called "superelastic" properties rather than its ability to undergo temperature-induced phase changes, although some phase change from austenite to stress-induced martensite may occur. In FIG. 5, the braided tube is positioned on a hollow plastic straw as representing a vein segment, and has been compressed axially to produce an increase in diameter. By extending the braided tube axially, as shown in FIG. 6, the tube becomes reduced in diameter to provide support to the vein segment.

The shape memory braided material shown in FIGS. 5 and 6, if used also for its phase transformation properties, may be supplied in a first configuration (which may be in the martensite phase) which can be easily manipulated to receive a vein segment 86 within the structure, and a second configuration (shown in FIG. 6, which may be in the higher temperature austenite phase) which has a "remembered" narrower diameter configuration to provide support to the vein segment. The contact of inner surfaces 170 of the structure with ablumenal surfaces 175 of the vein segment 86 is shown also in FIG. 7. The resilience of shape memory materials can be controlled by altering compositions, tempering procedures, wire diameters, etc., so that a tubular support fashioned from this material may mimic (when combined with the minimal mechanical values of a vein segment) the compliance values of a host artery in order to optimize the venous graft-artery interaction.

This aspect of compliance mimicking has components of expansion, recoil, timing, and tissue remodeling. In this example, the vein-stent compliance values are chosen to closely mimic those of a healthy native artery. Whereas the shape memory wires are shown as braided in these figures, they may also be knit, and in fact the knit configuration appears to be offer certain advantages.

Radially resilient tubular supports may be knit from metal wire, such as stainless steel and cobalt-chromium alloys. Metal wires ranging in diameter from about 25 to 150 micrometers are appropriate for knit supports with diameters in the range of 35 to 50 micrometers being particularly useful, although larger or smaller diameters may be employed as desired. For braided tubular supports, metal wires ranging in diameter from about 37 to about 170 micrometers are appropriate, although larger or smaller diameters may be employed.

Figure 21:
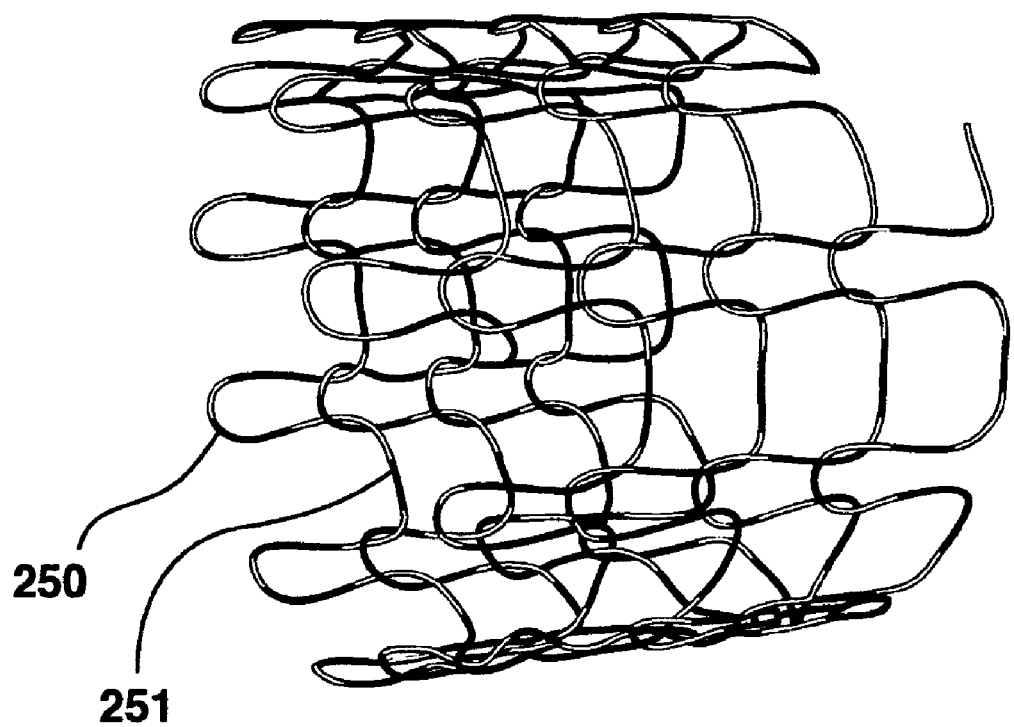
FIG. 21 is a photographic, perspective view of a section of a knit tubular support.

Knitting procedures may be performed by known methods using, for example, a LX96 knitting machine manufactured by the Lamb Knitting Machine Corporation. Favorable radial compliance and tubular dimensional properties may result from knitting the tubular structure in a manner providing loops that alternate in the circumferential direction between larger and smaller loops, as shown in FIG. 21. In this Figure, smaller loops 250 are shown alternating circumferentially with larger loops 251. Such alternating loop sizes typically present themselves visually as longitudinal stripes extending axially along the tubular support, as the adjacent loops of each size align in the longitudinal axis. Each closed end of the loop may be either rounded or generally square-shaped or variations in between, and, the sides of the loop may turn outward, be parallel, or turn inward. The latter design has shown some advantage in acting like a spring and assisting in the stability of the overall dimensions of the tubular structure, and maintaining its compliance characteristics.

Figure 17:
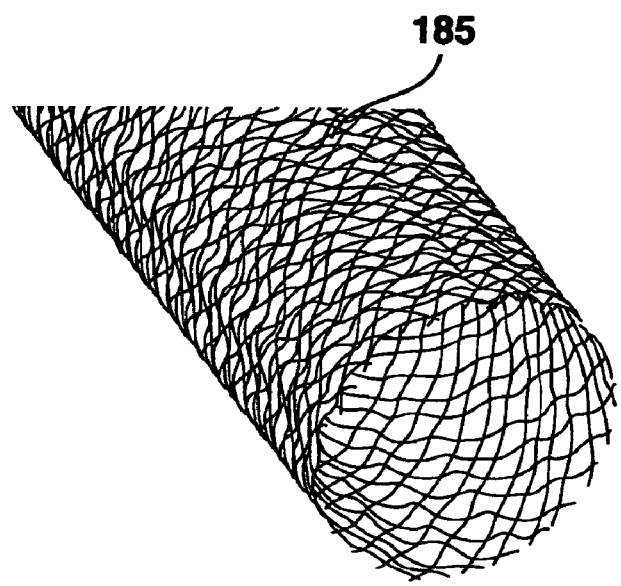
FIG. 17 is a broken-away, perspective view of a post-braiding crimped tubular support.

The knitted or braided tubular support may then be subjected to crimping to provide crimps extending, for example, about the circumference of the tubular support (that is, in the manner shown in FIG. 17). One way of doing this is through the use of an axially fluted mandrel that is inserted into the tube and is pressed outwardly against a wall of the tube to force the wall against a complementary shaped outer female mold to bend the knitted or braided wires and to form a circumferential crimp, the crimp resulting from each flute or raised ridge of the mandrel extending axially of the support.

A compliant venous graft using various metals or polymers for the tubular support may be provided in several ways. Embodiments may be advantageously provided in knitted form. FIGS. 8 and 9 show material 165 in a braided configuration, and FIGS. 10 and 11 show material 165 in a knitted configuration. Mechanical characteristics of the tubular support may be enabled by the type of shaping and relational structures formed on the elements making up the knit or braided structures. It is contemplated that a technique involving crimping of the material 165 to achieve angular crimps (shown in FIGS. 12 and 13), formed prior to the braid or knit construction, and rounded crimps (shown in FIG. 14) may provide acceptable results. Crimping techniques that may be appropriate with pre-knit configurations, are shown in FIG. 15 (angular crimps) and FIG. 16 (rounded crimps). Another technique for achieving certain performance characteristics of braided or knitted shape memory materials 165 is to perform crimping after braiding or knitting, i.e. post-braiding or post-knitting. FIG. 17 shows one embodiment of material 165 formed in a braided configuration and having a post-braided crimping operation applied to form a crowned pattern to achieve desired crimp characteristics.

Crimp angle and pitch density may be important variables in certain embodiments of the current design of the tubular supports. It is understood, however, that certain advantages of this invention may still be achieved without use of crimping. Ranges of crimp angle are preferably from about 10° to 85° to the line of lay of the reinforcing wire or braid. The crimp size may vary from 0.01 to 5 mm in length. It is desired that the braid or helical wires have a pitch angle that may vary from about 5-85° to the axial length of the vein graft.

Applicants have identified certain crimping techniques that relate to crimping either before or after braiding or knitting. For example, in post-braid crimping the material braids are produced according to existing techniques, after which macroscopic longitudinal crimping is imparted to the tubular mesh using a post-braid crimping tool. However, according to the material and specific configuration of the stent, if the post-braid crimping of braided tubes does not achieve sufficient compliance then alternate methods are possible. One example is to effect pre-braid crimping, thereby setting the memory of a shape memory material in a crimped configuration and subsequently straightening the material before braiding. The crimp is thus induced upon exposure to physiological temperatures.

The external tubular support adjusts the mechanical and geometrical properties of the vein graft to match or mimic healthy arterial properties and therefore adapt to the arterial pressure of the host artery. Accordingly, this results in substantial matching of the lumen of the vein graft and the host artery, the substantial matching of compliance of the vein graft and the host artery, and substantial matching of the radius to wall thickness ratio (r/wt) of the vein graft to the host artery. As noted above, optimization of the vein-stent compliance should ensure that the vein-stent graft mimics the behavior of arteries regarding the non-linear stiffening with increasing diameter due to elevated blood pressure, "locking" at a maximum pressure, and then demonstrating dynamic recoil in a timely manner.

Figure 18:
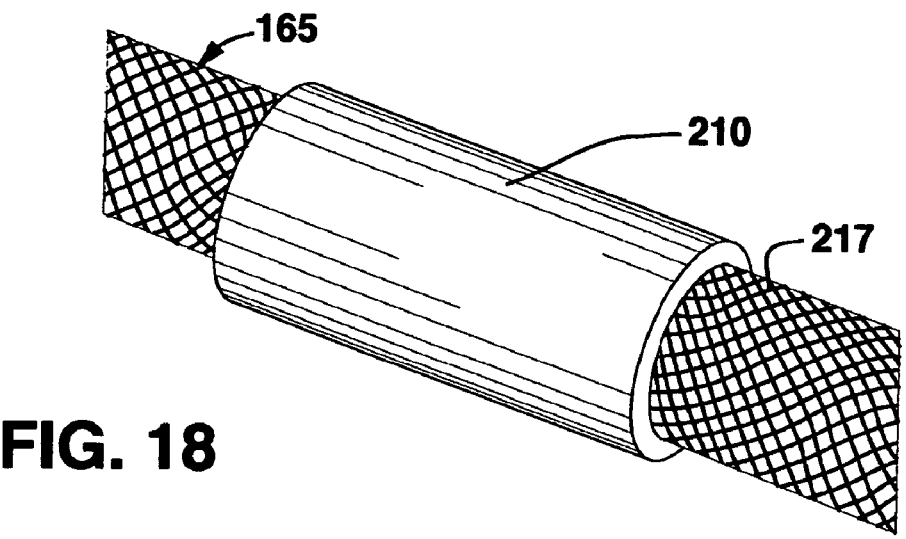
FIG. 18 is a broken-away, perspective view of a venous graft showing a portion with anti-fraying element.

When venous grafts utilizing knit or braided tubular supports are cut at angles suitable for end-to-end anastomoses, either at generally right angles or in scallop-like shape, the ends of the supports may experience fraying (see, for example, FIG. 17). Certain methods and structure are helpful to eliminate such fraying. In one embodiment, adjustable rings 210 of bioabsorbable or biodegradable material are placed generally circumferentially around a portion of the material 165, and in contact with external surfaces 217, as shown in FIG. 18. The number of rings may be varied as needed. The location of the rings may be adjusted to the position of anastomoses where vein and tubular support need to be cut. The cut or suture may be carried out through the ring, and the ring may be absorbed or degraded over a predetermined time, as desired.

Another embodiment of a structure to prevent fraying of a knit or braided tubular support when it is cut is the use of polymer coating for the fiber mesh. This feature may also provide the benefit of preventing gluing of joints and contact zones of elements of the stent. However, use of the radially compliant tubular support as a reinforcing structure may advantageously involve bonding of the ablumenal surface of a vein segment to confronting internal surfaces of the support. This attachment or connection may be accomplished through the use of a glue or other material having adhesive or connecting characteristics. In one embodiment, a fibrin glue or other material having adhesive or connective characteristics may be sprayed on designated portions of the vein (as exemplified at 283 in FIG. 20) and/or the tubular support. Another embodiment includes placement of a material on designated portions of the lumenal surfaces of the tubular support so as to provide the characteristics of contact adhesion and/or bonding when these portions contact the vein. However, the glue or other material must not inhibit the function of the tubular support. It is desirable that the contact of the tubular support with the ablumenal vein segment surface be reasonably uniform along the length of the support, and that regions of much higher force of the support against the ablumenal wall of the vein be avoided.

Figure 19:
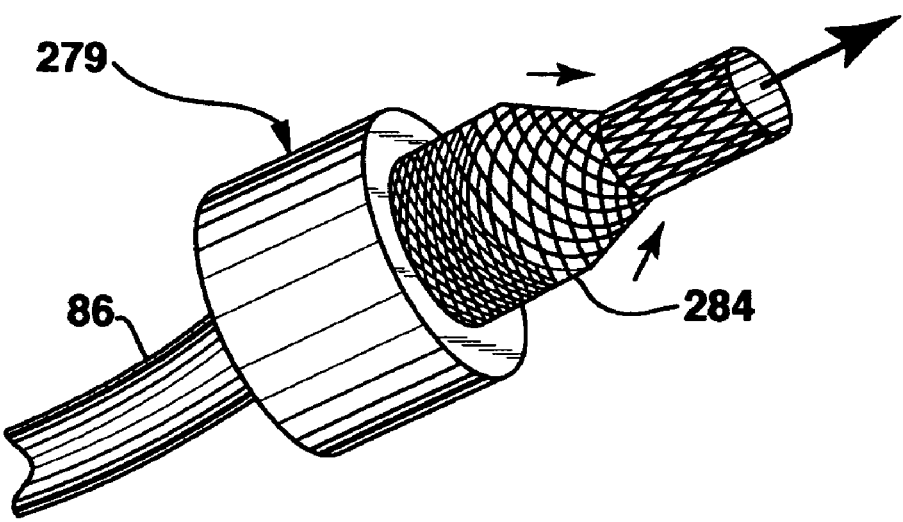
FIG. 19 is a broken-away, perspective view of one embodiment utilizing an applicator for assembling a venous graft.

Applicants have further recognized the need for a device to facilitate assembly of the radially compliant tubular support and a vein segment. It is desirable that such an applicator should not obscure the stent lumen, and that it should allow for easy insertion of the vein. It is further recognized that a design whereby diameter is increased by length compression, as in a braided configuration, would allow easy slipping of the tubular support over a vein. FIG. 19 illustrates this concept in combination with an applicator 279 to apply the braided support 284 to a vein 86. This longitudinal braid contraction phenomena (shown earlier in FIGS. 5 and 6), and which must be carefully managed at the time of joining the vein to the stent, is likely quite useful to achieving the goals of an applicator 279, as noted above. This applicator may also facilitate placement of anti-fraying rings 210. In one embodiment, the method of using the applicator comprises the steps of: providing the means of longitudinally contracting a stent; holding the stent in the contracted position with increased stent diameter resulting; inserting a vein into the stent lumen; and distending the stent longitudinally while the vein is inserted simultaneously until the stent is slipped over the desired portion of the vein. Further design considerations must ensure that the stent will not be fixed to the vein in a longitudinally over-distended or contracted state, so as to ensure that the predetermined mechanical stent properties remain viable.

Figure 20:
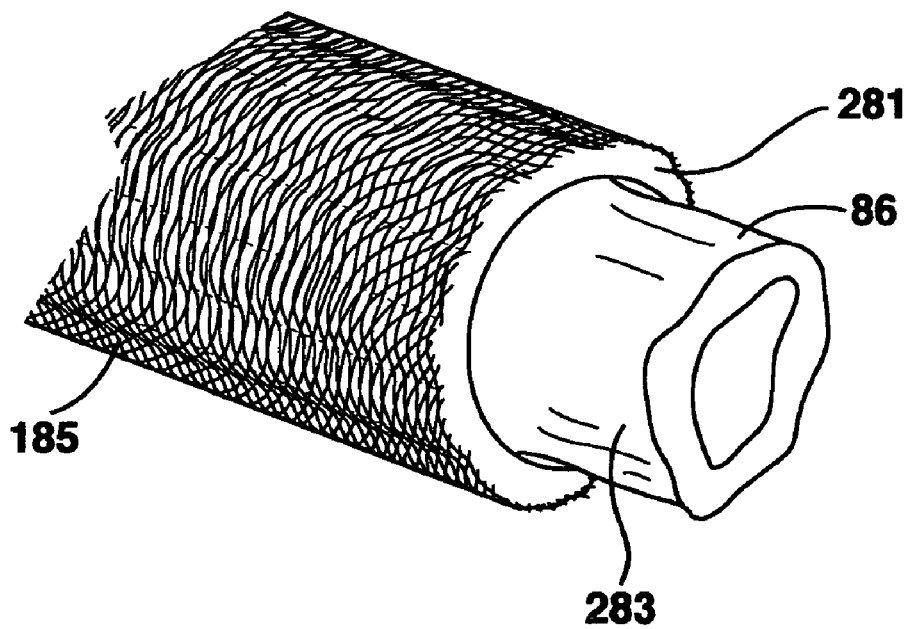
FIG. 20 is a broken-away, perspective view of the use of a modified applicator for assembling a venous graft.

FIG. 20 shows an embodiment in which a tubular support 185 is received along the outer surface of surface of an applicator 281 having an internal passage, and, while passing the vein segment 86 from within the applicator passage, the tubular support is drawn onto the ablumenal surface of the vein segment. The applicator here may be a thin walled tube resembling a soda straw.

It is important that the support be applied to a vein at a predetermined length which is associated with a particular desired compliance. A length-defining support feature or system should ensure a predetermined support length. This is particularly true with respect to braided supports, and perhaps less important with knit supports in which radial resilience is less dependent upon the amount to which the support is extended axially.

In a braided support, and to a much lesser extend in a knit support, compliance and related mechanical properties are linked to the support length through the pitch angle. Imparting a change in length results in a change in pitch angle and compliance. However, the compliance of the support is a mandatory characteristic which is optimized, as noted above, to mimic the compliance of a normal healthy host artery. When applying a support to a vein segment, it is important to accurately accommodate the predetermined tubular support length, even after longitudinal contraction of the support for the attachment of the support to the vein.

With braided, and to a much lesser extent knit supports, axial support length may be controlled, for example, through the use of an axially extending, relatively inextensible element, (as for example the thread 78 in FIG. 7), that restrains the tubular support from unwanted axial extension. The thread may be woven through the support mesh and may be fastened, as by welding, to the various wires that the thread encounters along the length of the support so that as the support is stretched axially, the extent of axial elongation is controlled by the thread as the thread is drawn taut. Moreover, this feature may enable a length of the tubular support to be divided into portions of appropriate length, with the permitted axial extension of each portion controlled by the section of thread within it. As presently envisioned, a vein segment may be sheathed in a tubular support as discussed in detail above, with the intent of cutting out a smaller segment of the resulting venous graft for use in the surgical replacement of an artery, and the venous graft that is thus used will have vein and tubular support ends that are coextensive.

Various generally tubular external wire mesh supports were fabricated from metal wires by braiding and by knitting, some being crimped and others not, and the diametrical compliance of each was measured using the in vitro diametrical compliance testing outlined above. The measured compliance values were dependent upon many variables, including wire size, tightness of braid or knit, etc. The following values were obtained:

| | Design | Compliance %/100 mm Hg |
|---|---|---|
| A | Braided Non-crimped | 0.9 |
| B | Braided Crimped | 5.6 |
| C | Braided Crimped | 1.8 |
| D | Knitted Non-crimped | 3.4 |
| E | Knitted Crimped | 7.9 |
| F | Knitted Crimped | 8.0 |
| G | Knitted Non-crimped | 10-21 |
| H | Knitted Non-crimped | 9-21 |
| I | Knitted Non-crimped | 16->30 |
| J | Knitted Non-crimped | >30 |
| K | Knitted Non-crimped | 10-16 |
| L | Knitted Non-crimped | 21-29 |
| M | Knitted Non-crimped | 22-28 |
| N | Knitted Non-crimped | >30 |
| O | Knitted Non-crimped | 10-15 |
| P | Knitted Non-crimped | 9-11 |
| Q | Knitted Non-crimped | 13-24 |
| R | Knitted Non-crimped | >30 |

A surgical procedure is proposed for use of the venous graft disclosed herein. This procedure, which may also be viewed as a simple method for placement of a venous reinforcement structure, includes, in this example, application of the compliant external tubular support during the procedure of vein excision. In many instances, vein excision is considered a standard part of a surgical operation, which is usually done by an assistant at a time when the surgeon is still in the preparatory phase of the operation.

In one embodiment, an initial step includes dissection and freeing of a saphenous vein. The saphenous vein is dissected free in a standard way, leaving it in situ while ligating and cutting off its branches. The second step involves testing for potential wall leaks of the vein. In order to test the isolated saphenous vein for potential leaks, it is normally cannulated distally and cold heparinised blood is injected while the proximal end is occluded. This inflation of the vein (using old techniques) with a syringe creates pressures of up to 350 mm of Hg and is often a main reason for traumatic damage of the vein wall. Therefore, a pressure limiting mechanism may be positioned between the vein cannula and the syringe. The external tubular support cannot be applied yet because leaks in the vein wall need to be freely accessible for repair. Therefore, no over-distention protection is placed around the vein yet, necessitating the limitation of the inflation pressure to a level suitable for detecting any leaks of concern but less than a level deemed to cause unacceptable damage, such as, for example, in one embodiment, 15 mm of Hg, the pre-maximal dilatation pressure for veins. The tissue remodeling functions of applicants' invention become more critical in view of the importance of leak testing and the reality of possible damage to the intimal layer in the vein during even the most carefully performed leak testing.

The next step involves assembling the harvested vein segment and an external tubular support of this invention. In this step, the tubular support (typified here as a knit support) is mounted on a tube or straw-like applicator within which is positioned the vein segment. See FIG. 20. The straw is then removed axially, leaving the support and vein in contact to form the venous graft. Over-extension of the tubular support is prevented using a length-limiting central thread or other means, as described above. As required, the vein segment is then inflated under arterial blood pressures of 120 mm of Hg, causing it to contact the tubular support inner lumenal surfaces. In certain embodiments, an adhesive securing the tubular support to the vein will ensure that the vein does not collapse during the surgical procedure when no internal pressure is applied. Again, it should be recognized (without limitation) that this is one of several ways to accomplish the above objectives.

The following sequence may occur at this or another time during the procedure. One of the external anti-fraying rings or cuffs is slid to the end of the vein, and a typical double-S-cutting line is used to prepare the end for the first anastomoses. The thin cuff prevents fraying of the tubular support and also gives the vein tissue and tubular support a uniformity which makes the surgical process of stitching the vein to the host artery in an end-to-side fashion much easier. Another thin anti-fraying ring is then slid down from the applicator to a position where either a side-to-side anastomoses for a sequential graft is being performed, or where the vein is being cut at an appropriate graft length. The half of the sliding cuff which remains on the original vein will make the process of the anastomoses to the proximal host artery much easier. In the case of a coronary artery bypass graft, for example, the end of the remaining vein protected by the other half of the cuff is used for the next distal graft anastomoses.

As structures have become increasingly complex, not only in design but also in the range of material use, pure analytical methods have begun to fail in describing the behavior of such structures. Due to the scientific challenge of closely matching a vascular graft of the type described herein to a host, analytical methods are rendered somewhat obsolete. Development of a prosthetic vascular graft which mimics the mechanical requirements and dynamic compliance of a normal healthy artery is made possible, however, with certain old tools, particularly cut and try methods in which incremental changes are made to the material or structure of the tubular support to modify its compliance properties, and the resulting properties are used to guide further changes. Empirical data or constitutive equations and mathematical analyses may be used for certain features. Alternatively, the use of numerical modeling with such tools as, for example, Finite Element Models and Methods, relying on continuum mechanics, along with certain other tools makes this level of customization feasible.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

What is claimed is:

1. A flexible, resilient, generally tubular external support within which may be supported a vein segment to form a replacement venous graft mimicking the compliance properties of a healthy artery, the tubular support comprising a knit wire mesh and being capable of resilient radial expansion in a manner providing compliance in the range of 3 to 30%/100 mm Hg.

2. The tubular external support of claim 1 wherein the vein segment includes an abluminal surface in contact with, and supported by, said knit wire mesh.

3. The tubular external support of claim 1 in which said knit wire mesh comprises loops that alternate in size circumferentially about the support.

* * * * *